United States Patent [19]

Schiller

[11] 4,227,805

[45] Oct. 14, 1980

[54] FINGER IDENTIFICATION APPARATUS AND METHOD

[76] Inventor: Michael Schiller, 4465 Douglas Ave., Riverdale, N.Y. 10471

[21] Appl. No.: 872,263

[22] Filed: Jan. 25, 1978

[51] Int. Cl.³ .......................... G06K 9/00; G06K 9/76
[52] U.S. Cl. ............................... 356/71; 340/146.3 E; 340/146.3 P
[58] Field of Search .................... 356/71, 209, 388; 340/146.3 E, 146.3 P, 146.3 Q; 250/566, 568; 350/162 SF

[56] References Cited

U.S. PATENT DOCUMENTS

| | | | |
|---|---|---|---|
| 3,196,392 | 7/1965 | Horwitz et al. | 340/146.3 P |
| 3,597,045 | 8/1971 | Mathisen | 340/146.3 P |
| 3,716,301 | 2/1973 | Caulfield et al. | 356/71 |
| 3,864,042 | 2/1975 | Leventhal | 356/71 |

FOREIGN PATENT DOCUMENTS 1204713  9/1970  United Kingdom .............. 340/146.3 P

OTHER PUBLICATIONS

Eleccion, M. "Automatic Fingprint Identification" IEEE Spectrum, 9-1973, p. 36.

Primary Examiner—John K. Corbin
Assistant Examiner—Wm. H. Punter
Attorney, Agent, or Firm—McAulay, Fields, Fisher, Goldstein & Nissen

[57] ABSTRACT

A slit beam of coherent light is scanned across a flat finger print or fingerpress to provide a modulated reflected light beam. A Fourier transform of the modulated light beam is projected onto a hologram of a standard character plate. The character plate, from which the hologram is made, contains standardized minutia; specifically, line bifurcations and line endings, that are typical of a finger surface image. Correspondence between one of the minutia being scanned and one of the minutia in the character plate results in correlation of the Fourier transform of the minutia being scanned with the hologram of the corresponding minutia on the character plate to produce a correlation beam. An array of photocells is placed optically downstream from the hologram. Excitation of one of the photocells by one of the correlation light beams serves to identify the minutia being scanned by type of minutia, position of minutia and angular orientation thereof.

16 Claims, 4 Drawing Figures

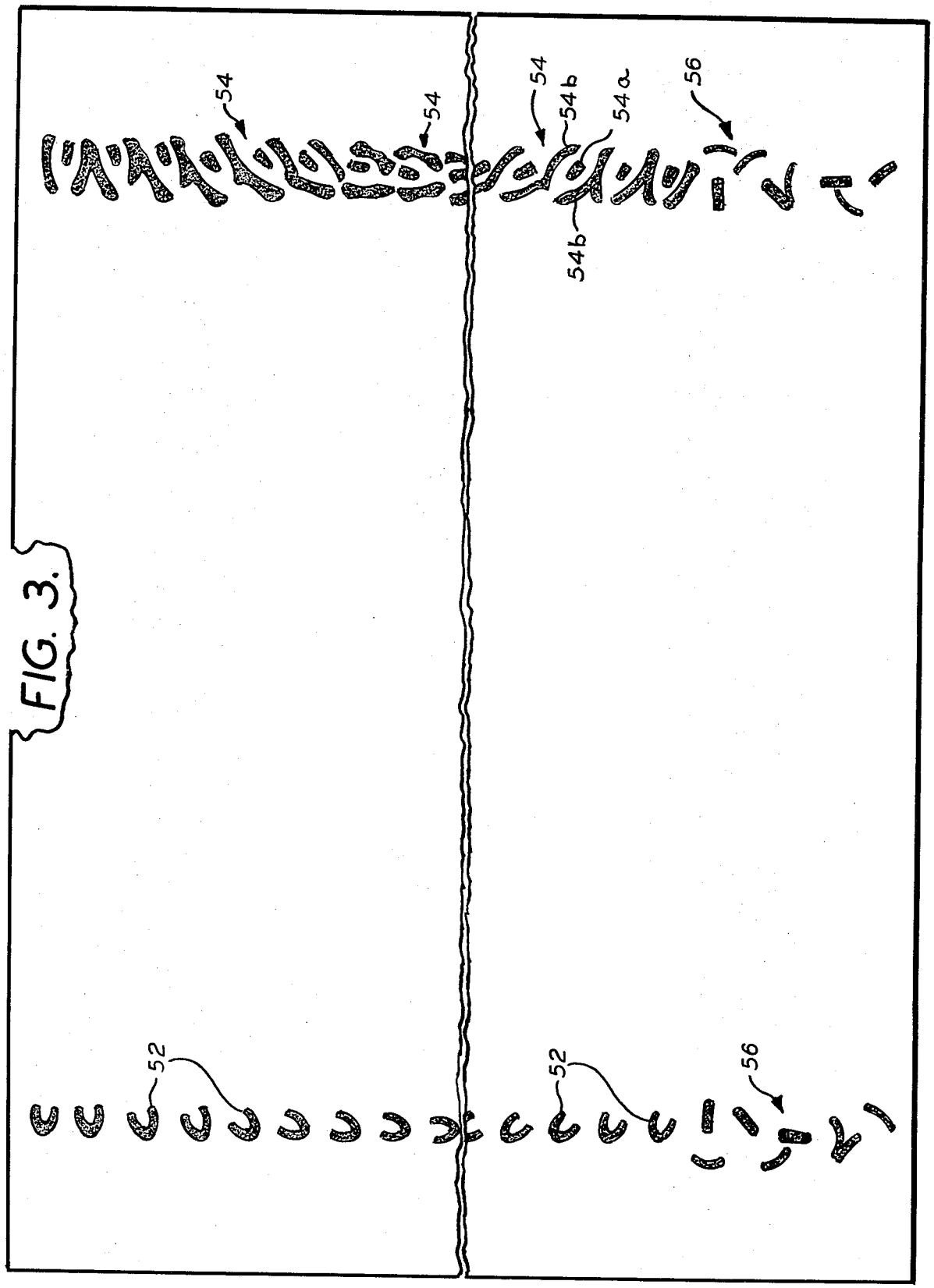

FINGER IDENTIFICATION APPARATUS AND METHOD

BACKGROUND OF THE INVENTION

This invention relates in general to techniques of identifying an individual by means of the unique pattern of ridges and valleys that are approximated by a fingerprint.

It has been recognized in the art that the pattern of line endings and line bifurcations in each of the finger ridges or valleys provide a unique set of what are called minutia. The pattern of the type of minutia, location of minutia and angular orientation of minutia is unique for each finger. An image of the surface of the finger can be provided on a flat plane, that image can be scanned in order to identify each minutia being scanned. Electronic techniques for doing this are complex and expensive. The finger image can be scanned and electronically processed to provide an identification of each minutia as to type of minutia, position in the finger image and angular orientations of minutia. As a practical matter, the costs of doing so are too prohibitive for all but in the rarest applications.

Accordingly, it is a major purpose of this invention to provide an inexpensive, simple and reliable technique for accurately identifying the minutia of a finger image.

It is important that the technique provide a minumum error rate in identification. Complex identification electronics tends to produce occasional erratic results which increase the identification error rate. Accordingly, another purpose of this invention is to provide a technique that is sufficiently reliable so that the error rate is minimal.

From the point of view of both costs and convenience it is important that the speed with which a finger or finger image being scanned is processed to provide the minutia identifying elements be as fast as possible. Accordingly, it is important that any simple, inexpensive and reliable technique meet at least the electronic processing speeds.

BRIEF DESCRIPTION

The most distinctive features of a fingerprint or fingerpress, as defined herein, are certain line endings and line bifrurcations. These elements are referred to as minutia. The position and orientation of the set of minutia associated with any given fingerprint or fingerpress provides a unique identification of the individual having that fingerpress. Thus identification of the set of minutia can be effective to provide a unique identification of the individual involved.

In brief, in the identification apparatus, a beam of coherent light scans across a fingerprint or across a finger that is pressed against a flat transparent glass plate. The beam is shaped to be 30 mm long and 1.5 mm wide. Thus a single sweep of the beam across the finger provides a complete scan. The scanning beam is modulated by the finger pressed against the glass plate to provide a modulated coherent light beam. A fourier transform of the modulated light beam is correlated against a hologram of a standard character plate.

The standard character plate from which the hologram is formed is a character plate of a set of standardized fingerprint minutia. These minutia are substantially line bifurcations and line endings. The hologram is formed in an off-axis manner so that in the identification apparatus, it constitutes part of an off-axis holographic correlator. A square matrix of 10,000 photo diodes is employed as the identification plate. During the scan of the finger, each correlation between a minutia being scanned and a minutia on the character plate, generates a correlation beam to provide a correlation spot on the diode plate. Each diode that provides an output will thereby indicate which of the minutia on the character plate corresponds to the particular minutia being scanned and will also indicate where within the scan line that minutia is located. A correlation reading is taken once each one-twentieth of a millimeter of travel of the scanning beam. The correlation readings are stored and can later be used to reconstruct the minutia or to provide the basis for automatic electronic identification.

BRIEF DESCRIPTION OF THE DRAWINGS

FIG. 3 illustrates the character plate used for forming the hologram employed in the FIG. 1 system. The character plate illustrated includes thirty-two different angular orientations of line bifurcations, thirty-two different angular orientations of line endings and eight special minutia.

DESCRIPTION OF THE PREFERRED EMBODIMENTS

Figures 1, 4:
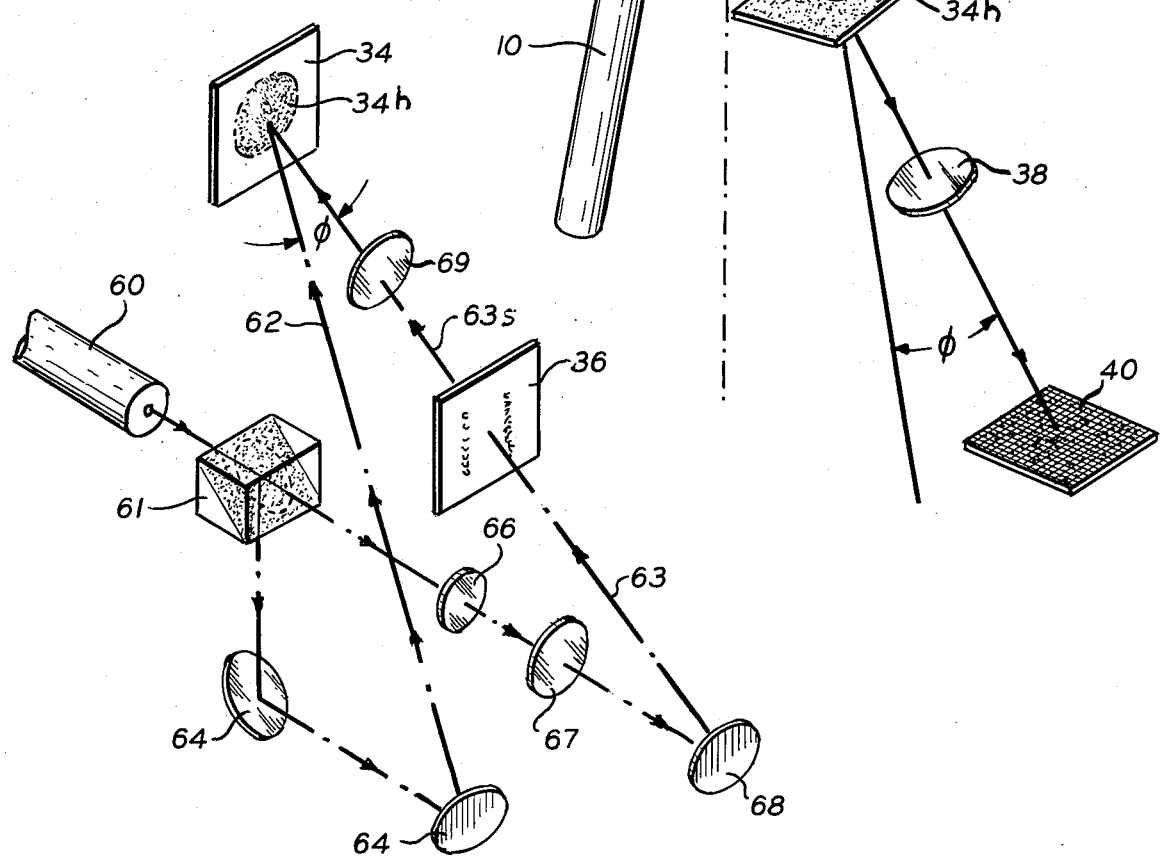
FIG. 1 is an optical and mechanical schematic of an embodiment of this invention.
FIG. 4 illustrates one technique of fabricating the hologram used in the FIG. 1 system from the FIG. 3 character plate.

As shown in FIG. 1, the system of this invention employs a laser 10 that provides a beam of coherent light. Cylindrical lenses 12 and 14 in the path of the laser beam are employed to shape and collimate the laser beam so as to provide an interrogating beam 16 which has the format of a slit. The laser 10 output is a beam having a circular cross section that is slightly over 1 mm in diameter and which would expand to about 1.5 mm in diameter at the site of the finger F. The cylindrical lenses 12 and 14 however cause the beam to be stretched out in one direction thereby providing an interrogating beam 16 that is approximately 30 mm along an X axis (perpendicular to the plane of FIG. 1) and 1.5 mm in a Y axis (a horizontal line in the plane of FIG. 1). The finger F of the individual to be identified is pressed on the top surface of a transparent glass platen 18 thereby forming a flat image which is called herein a fingerpress. The platen 18 is held on a carriage 20, which carriage 20 is movable along the Y axis (that is, along a horizontal line in the plane of FIG. 1). The platen is movable within the limits of a recess 22 in the support member 24.

In operation, the finger F is placed on the platen 18, the tip of the finger abutting against the end stop 26 of the carriage 20. The slitted beam 16 is positioned so that it will impinge on the forward end of the fingerpress when the elements are in the initial relationship shown in FIG. 1. Thereafter the finger exerts a continuous pressure in a forward direction (to the right as seen in FIG. 1) thereby causing the carriage 20 to move to the right to approximately the position shown in phantom in FIG. 1. As the carriage 20 moves, its speed is limited by a speed limiting mechanism 28. As the carriage 20 and thus the fingerpress on the platen 18, moves to the right it will be moving relative to the stationary interrogating slit-shaped beam 16. In this fashion, the slit beam 16 will be scanning the fingerpress along the Y axis. Because the slit beam 16 extends the full length of the fingerpress in the X axis, the entire fingerpress will thereby be scanned during a single action of the finger F and platen 18 in moving forward between the two positions shown in FIG. 1. The light beam 30 that is reflected from the top surface of the platen 18 is modulated with fingerpress information.

The modulated lightbeam 30 is optically processed downstream by an optical correlator. The optical correlator consists essentially of (a) a first lens 32, which takes the Fourier transform of the modulated lightbeam, (b) a hologram plate 34 which contains a hologram 34h of a predetermined character plate, (c) a second lens 38 and (d) an identification array 40 which consists essentially of 10,000 photodiodes arranged in a square matrix of 100 diodes on a side.

The lens 32, which in one embodiment is a lens having a 200 mm focal length, is positioned so that its frontal focal plane is at the top surface of the platen 18 and its back focal plane is at the plane of the hologram plate 34. Thus the Fourier transform provided by the lens 32 is projected on the hologram 34h carried by the hologram plate 34. The hologram 34h, which is generated by the optical arrangement shown in FIG. 4 is an off-axis hologram of the character plate illustrated in FIG. 3.

A description, in somewhat greater detail, of the operation of the off-axis optical correlator is provided in U.S. Pat. No. 4,053,228.

Suffice it to say here that when an element being scanned is the same as an element on the character plate, the Fourier transform of the reflected image of that element at the hologram plane 34 will interact with the hologram 34h of that element to provide a correlation beam which is projected onto the identification plane 40.

The term fingerpress is used herein as defined in U.S. Pat. No. 4,053,228 to refer to the surface configuration of valleys and crests that is created when a finger is pressed against a smooth transparent glass plate surface. The fingerpress thus represents the actual configuration of the surface of a subject's finger more closely than does the image provided by the typical fingerprint. It should be understood however that this invention can be employed with the less refined fingerprint. The fingerpress is preferred and will be used herein. But it should be understood that the term fingerpress in the claims includes what is known as a standard fingerprint or any other approximation of the configurations of the hills and valleys on an individual's finger. What is required in this invention is that a distinctive number of minutia are displayed for interrogation by the system of FIG. 1.

Figure 2:
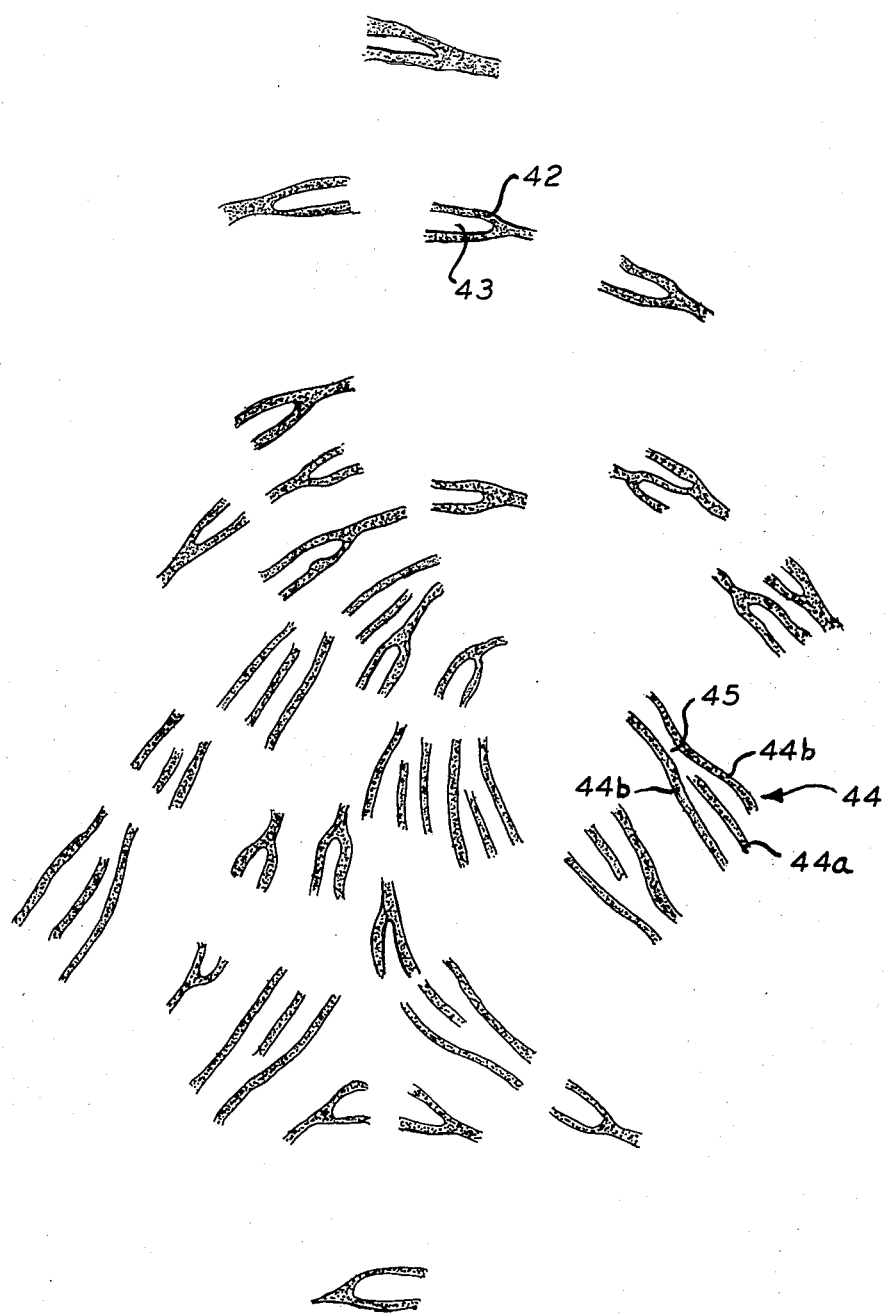
FIG. 2 illustrates the minutia; specifically, bifurcations and line endings, of a typical fingerpress or fingerprint.

FIG. 2 is abstracted from a typical fingerpress in which all lines are removed except the lines adjacent to a bifurcation or surrounding a line ending. In FIG. 2, the bifurcation 42 is a typical bifurcation. It is where a valley or a ridge bifurcates. In FIG. 2 the configuration 44 represents a typical line ending. The line 44a simply terminates. Its identification as a line ending requires association with two lines 44b surrounding it which are continuous in the area of line 44a termination. These minutia 42 and 44 may be either ridges or valleys. In the embodiment that has been built and tested they are valleys. It should be noted that each valley bifurcation 42 serves to define a ridge ending. Similarly, each valley ending 44 is defined by a ridge bifurcation. Thus the bifurcated valley 42 defines a ridge 43. The valley ending 44 is defined by a bifurcated ridge 45. The line bifurcations and line endings of a fingerprint have been found to be sufficiently standard so that a standardized line bifurcation, such as the elements 52 in FIG. 3 and a standardized line ending pattern such as the patterns 54 in FIG. 3 will serve to correlate with line bifurcations and line endings in all fingerprints.

The character plate 36, illustrated in FIG. 3, contains a series of standarized characters. On the left hand side of the plate are thirty standardized bifurcation characters 52 each of which is identical to the other except that each one is rotated 12° relative to the adjacent ones. These bifurcation lines 52 provide a reference that will correlate with most bifurcations on the fingerpress and thus ultimately produce a signal at the identification array 40. On the right hand side of FIG. 3, are thirty standardized lines endings 54, each of which is identical in size and aspect except that each is rotated 12° relative to the following or preceeding line ending. The line endings 44 are characterized by a line 54a which ends and which is surrounded by two other lines 54b. In addition there are eight special minitia 56 that are used to further facilitate identification and provide additional correlation.

The thickness of the minutia lines displayed on the FIG. 3 character plate define what will be deemed as identifying minutia for the purposes of this invention. For example, the aspect of the bifurcations 52 shown on the left hand portion of the FIG. 3 character plate in effect defines a window. Any bifurcation on the fingerpress which substantially fits in that window will establish a correlation that will provide a hit on the diode array 40 and thus establish one identification point for the fingerpress being examined. A configuration on the fingerpress which may appear to be a bifurcation but which does not fit substantially within that window and thus does not establish a correlation will not be, for the purposes of this embodiment, a bifurcation. At least, it will not be one of the minutia that serves to provide identification or verification. In effect, the window defines the minutia.

To generate the character plate shown in FIG. 3, a single average or typical bifurcation minutia and a single average or typical line ending minutia is selected from an examination of a large number of fingerprints. The minutia lines are about one mm thick. A mask of the minutia is then fixed in position and rotated plus and minus 6°. All of the area covered by the opening in the mask during that twelve degrees of rotation is employed as the standardized identification minutia character for the FIG. 3 character plate. The result of this rotation technique can be seen somewhat by an examination of the line ending minutia on the right hand side of the FIG. 3 plate. The inboard end of the line 44a is taken as the center of rotation of the standardized minutia. The rotation for each position of the minutia 44 causes the surrounding line segments 44b to be slightly thicker at their ends than at the center. This can be seen in FIG. 3. By developing the minutia for the character plate in this fashion, correlation is assured with each minutia scanned in the fingerpress regardless of the angular orientation of that minutia.

Because of the elemental nature of the minutia, a fairly substantial variance in scale factor and even in rotation can be tolerated while retaining the ability to identify the minutia involved.

In order to achieve correlation between the minutia of the finger being scanned and the minutia of the hologram it is essential that the surface of the hologram plate 36 and the surface of the platen 18 both be extremely flat. It is desirable that the surfaces be flat within a quarter of a wavelength. Correlating the minutia of the fingerpress against the hologram of the minutia from a planar character plate 36 requires that the fingerpress be perfectly flat. Low spatial frequency inputs due to variatons in the surface will throw the correlation off. There are known techniques for obtaining the required flatness. One preferred technique is to procure a platen 18 that is extremely flat on one surface; preferably within a quarter of a wavelength. The other surface of the platen is filled with an epoxy and the surface of that epoxy is formed through contact with a glass master that has the desired flatness. The epoxy is about one-fortieth of a mm thick. The result is to provide the preferred plastic surface as described in applicant's copending patent application Ser. No. 844,580 filed on Oct. 25, 1977 and entitled "Fingerprint Processing Apparatus".

At the plane 40, a photodiode is turned on by the correlation beam to provide an output signal indicative of the minutia being scanned. Because the scannning beam 16 is a slit beam, a number of minutia will be identified simultaneously each time a reading is taken. Thus, normally a plurality of correlation light beams are formed simultaneously and a number of photodiode output signals are provided simultaneously.

In the embodiment described, the minutia on the character plate of FIG. 3 are represented by transparent areas. These minutia will correlate with corresponding valley areas on the fingerpress. Thus it is valley endings and valley bifurcations which are correlated to provide verification and identification. However with an adjustment in the optics employed, ridge endings or ridge bifurcations could be the minutia employed. Accordingly, the minutia are referred to herein as line endings and line bifurcations; it being understood that the lines could be either all ridges or all valleys.

The vertical position of the minutia on the character plate 36 of FIG. 3 will determine the position along the Y axis in the diode array 40 where a correlation spot will appear. The position along the X axis in the diode array 40 where the correlation spot will hit is determined by where the corresponding minutia appears along the scan line. However, with respect to a given scan line, the relative positions along the X axis of the array 40 of the minutia being identified is a reversal of the relative position of the corresponding minutia on the fingerpress being scanned. Those minutia represented on the right hand edge of the FIG. 3 character plate 36 will all have their corresponding correlation spots on the right half of the diode array 40. Similarly, all those minutia represented on the left hand edge of the character plate 36 will have their respective correlation spots appear on the left half of the photodiode array 40.

One technique of generating the hologram 34h on the hologram 34 is described in said U.S. Pat. No. 4,053,228 and in particular is shown in connection with FIG. 6 of that patent. FIG. 4 herein is very similar to FIG. 6 of said patent and is illustrated primarily for convenience. In brief, with reference to FIG. 4, a laser 60 having exactly the same frequency as the laser 10 in FIG. 1, provides a coherent light beam which is split by a beam splitter 61 to provide a reference beam 62 and in interrogating beam 63. Mirrors 64, 68 provide nothing more than a steering function. The lenses 66 and 67 provide the function of expanding and collimating the interrogating beam 63. The interrogating beam 63 passes through the predetermined FIG. 3 character plate 36 and thereby provides a modulated beam 63a. Lens 69 effects a Fourier transform of the diffracting modulated beam 63s and thereby provides a fully diffracted image at the back focal plane of the lens 69. Identification plate 34 is placed at this back focal plane of the lens 69 so that a film negative held by the plate 34 will produce the hologram 34h by virtue of the interaction of the reference beam 62 and the diffracted image at the plane of the plate 34.

In one embodiment that has been tested the scanning beam 16 is 1.5 mm wide and 30 mm long. The minutia lines on the fingerpress tend to be about 1 mm thick. During the test scan, a reading was taken once for each one-twentieth of a millimeter of finger F travel. Thus, in scanning across a single fingerpress, about 250 separate readings are taken. At each of the 250 equally spaced readings, the field of photodiodes 40 is read and the results stored. At the end of the scan, information is thus available which permits reconstructing all of the minutia in place and with a proper orientation. In effect, the FIG. 2 illustration can be constructed. As a practical matter, a substantially coarser reading interval would work and provide the FIG. 2 illustration or the equivalent thereof. Furthermore, the information stored can be processed electronically for the purpose of effecting a comparison against comparable stored information for the party involved so as to provide a verification check.

Although scale factors may effect how many photoreceptors are excited on the plate 40 by a correlation beam, it is a simple matter for the electronics downstream from the identification array 40 to include a means for selecting a particular location on the array as the one representing scan line position and minutia orientation. For example if the correlation beam at the surface of the array 40 has a diameter equal to the span of three photo-receptors, the center photo-receptor can be selected as the one properly indicative of the minutia involved.

What I claim is:

1. Fingerpress processing apparatus comprising:

scanning means to scan an interrogating beam of spatially coherent light having a predetermined cross sectional shape across a fingerpress to provide a reflected light beam modulated with minutia identification information, a holographic correlator coupled to said reflected light beam, said correlator including a hologram of a predetermined character plate having a plurality of standardized finger identification minutia, said minutia including a first set of bifurcation minutia and a second set of line ending minutia, each of the bifurcation minutia in the first set being identical to one another in shape and having an angular orientation unique relative to all other bifurcation minutia, each of said line ending minutia being identical to one another in shape and having an angular orientation unique relative to all other line ending minutia, each of said standardized minutia having a predetermined spatial position on said character plate, and projection means to project the Fourier transform of said reflected light beam onto said hologram to provide a plurality of correlation light beams indicative of the minutia being scanned on said fingerpress.

2. The apparatus of claim 1 further comprising:
a platen 18 having a back surface on which said fingerpress is applied, said back surface being sufficiently flat to assure correlation with the minutia of said predetermined character plate.

3. The apparatus of claim 1 wherein said predetermined character plate has a first column of bifurcation minutia and a second column of line ending minutia, said columns being spaced from and substantially parallel to one another, each of the bifurcation minutia in said first column being identical to one another in shape and having an angular orientation unique relative to all other bifurcation minutia, each of said line ending minutia being identical to one another in shape and having an angular orientation unique relative to all other line ending minutia.

4. The apparatus of claim 3 further comprising:
a platen 18 having a back surface on which said fingerpress is applied, said back surface being sufficiently flat to assure correlation with the minutia of said predetermined character plate.

5. The apparatus of claim 1, wherein each of said standardized minutia on said character plate are formed by rotating a typical minutia through a predetermined angle to provide a standardized identification minutia character adequate to correlate with corresponding minutia on the fingerpress over said predetermined degree of rotation.

6. The apparatus of claim 2, wherein each of said standardized minutia on said character plate are formed by rotating a typical minutia through a predetermined angle to provide a standardized identification minutia character adequate to correlate with corresponding minutia on the fingerpress over said predetermined degree of rotation.

7. The apparatus of claim 3, wherein each of said standardized minutia on said character plate are formed by rotating a typical minutia through a predetermined angle to provide a standardized identification minutia character adequate to correlate with corresponding minutia on the fingerpress over said predetermined degree of rotation.

8. The apparatus of claim 4, wherein each of said standardized minutia on said character plate are formed by rotating a typical minutia through a predetermined angle to provide a standardized identification minutia character adequate to correlate with corresponding minutia on the fingerpress over said predetermined degree of rotation.

9. Fingerpress processing apparatus comprising:
a source of spatially coherent light providing an interrogating beam having a predetermined cross sectional shape,
scanning means to scan said interrogating beam across a fingerpress to provide a reflected light beam modulated with identification information, and
an off-axis holographic correlator coupled to said reflected light beam,
said correlator including a hologram of a predetermined character plate having a plurality of standardized finger identification minutia, said minutia including a first set of bifurcation minutia and a second set of line ending minutia, each of the bifurcation minutia in the first set being identical to one another in shape and having an angular orientation unique relative to all other bifurcation minutia, each of said line ending minutia being identical to one another in shape and having an angular orientation unique relative to all other line ending minutia, each of said standardized minutia having a predetermined spatial position on said character plate,
said correlator including an identification plate having a two dimensional array of photo-receptors, each of said receptors having a first state and a second state,
the correlation of a minutia being scanned on said fingerpress with a corresponding minutia of said predetermined character plate providing a light signal sufficient in intensity to change the state of at least one of said photoreceptors,
whereby each minutia in the fingerpress being scanned is identified as to kind, location and orientation.

10. The apparatus of claim 9 further comprising:
a platen 18 having a back surface on which said fingerpress is applied, said back surface being sufficiently flat to assure correlation with the minutia of said predetermined character plate.

11. The apparatus of claim 10 wherein said predetermined character plate has a first column of bifurcation minutia and a second column of line ending minutia, said columns being spaced from and substantially parallel to one another, each of the bifurcation minutia in said first column being identical to one another in shape and having an angular orientation unique relative to all other bifurcation minutia, each of said line ending minutia being identical to one another in shape and having an angular orientation unique relative to all other line ending minutia.

12. The apparatus of claim 11, wherein each of said standardized minutia on said character plate are formed by rotating a typical minutia through a predetermined angle to provide a standardized identification minutia character adequate to correlate with corresponding minutia on the fingerpress over said predetermined degree of rotation.

13. The method of identifying a fingerpress comprising the steps of:
scanning said fingerpress with an interrogating beam of spatially coherent light having a predetermined cross-sectional shape to provide a reflected light beam modulated with identification information, and
correlating the minutia images carried by said reflected light beam against a plurality of predetermined standardized finger identification minutia from a character plate having a plurality of standardized finger identification minutia, said minutia including a first set of bifurcation minutia and a second set of line ending minutia, each of the bifurcation minutia in the first set being identical to one another in shape and having an angular orientation unique relative to all other bifurcation minutia, each of said line ending minutia being identical to one another in shape and having an angular orientation unique relative to all other line ending minutia, each of said standardized minutia having a predetermined spatial position on said character plate, said step of correlating including projecting the Fourier transform of said reflected light beam on a hologram of said character plate to provide correlation light beams representative of each correlation obtained.

14. The method of claim 13 further comprising the step of:
   projecting said correlation light beams onto an array of photo-receptors to provide a plurality of output signals indicative of minutia type, position and angular orientation.

15. The method of claim 13 further comprising the step of:
   forming said standardized finger identification minutia from the area covered by rotating typical minutia over a predetermined number of degrees.

16. The method of claim 14 further comprising the step of:
   forming said standardized finger identification minutia from the area covered by rotating typical minutia over a predetermined number of degrees.

* * * * *